United States Patent
Dumont et al.

(10) Patent No.: US 9,323,973 B2
(45) Date of Patent: Apr. 26, 2016

(54) DEVICE FOR CAPTURING AN IMAGE REPRESENTING A PRINT OF A PART OF THE BODY OF A PERSON

(71) Applicant: MORPHO, Issy-les-Moulineaux (FR)

(72) Inventors: Denis Dumont, Issy-les-Moulineaux (FR); François Rieul, Issy-les-Moulineaux (FR); Michel Cruchaga, Issy-les-Moulineaux (FR); Sylvaine Picard, Issy-les-Moulineaux (FR)

(73) Assignee: MORPHO, Issy-les-Moulineaux (FR)

( * ) Notice: Subject to any disclaimer, the term of this patent is extended or adjusted under 35 U.S.C. 154(b) by 0 days.

(21) Appl. No.: 14/434,146

(22) PCT Filed: Jun. 5, 2014

(86) PCT No.: PCT/EP2014/061753
§ 371 (c)(1),
(2) Date: Apr. 8, 2015

(87) PCT Pub. No.: WO2014/195429
PCT Pub. Date: Dec. 11, 2014

(65) Prior Publication Data
US 2015/0288879 A1   Oct. 8, 2015

(30) Foreign Application Priority Data

Jun. 7, 2013 (FR) ..................... 13 55256

(51) Int. Cl.
*G06K 9/00* (2006.01)
*H04N 5/225* (2006.01)
*A61B 5/117* (2006.01)

(52) U.S. Cl.
CPC ............ *G06K 9/0004* (2013.01); *G06K 9/0002* (2013.01); *H04N 5/2256* (2013.01); *A61B 5/1172* (2013.01)

(58) Field of Classification Search
CPC .......... G06K 9/00006–9/0012; H04N 5/2256; A61B 5/1172; G06F 2203/0336–2203/0338; B60R 25/252
See application file for complete search history.

(56) References Cited

U.S. PATENT DOCUMENTS

| | | | |
|---|---|---|---|
| 2004/0201739 A1* | 10/2004 | Kuwayama | H04N 5/232 348/231.3 |
| 2005/0213799 A1* | 9/2005 | Sawano | G06K 9/0002 382/124 |

(Continued)

FOREIGN PATENT DOCUMENTS

| | | |
|---|---|---|
| EP | 0901093 A2 | 3/1999 |
| EP | 1316913 A2 | 6/2003 |
| WO | 2008/052017 A2 | 5/2008 |

OTHER PUBLICATIONS

Jul. 15, 2014 Search Report issued in International Application No. PCT/EP2014/061753.

*Primary Examiner* — Dennis Hogue
(74) *Attorney, Agent, or Firm* — Oliff PLC; R. Brian Drozd

(57) ABSTRACT

A device for capturing an image representing a print of a part of the body of a person, the capture device may include: a base layer; a reference electrode covering the base layer; electronic capsules fixed in the form of a matrix on the reference electrode, each electronic capsule consisting of a microcapsule filled with a liquid medium and particles with two different colors and opposite electrical charges; a support plate covering the electronic capsules and serving as a support for said part; a camera intended to take an image of the electronic capsules; and an active electrode intended to come into contact with said part and electrically connected to a voltage source delivering a non-zero electrical voltage.

13 Claims, 2 Drawing Sheets

(56) References Cited

U.S. PATENT DOCUMENTS

Figure 1:
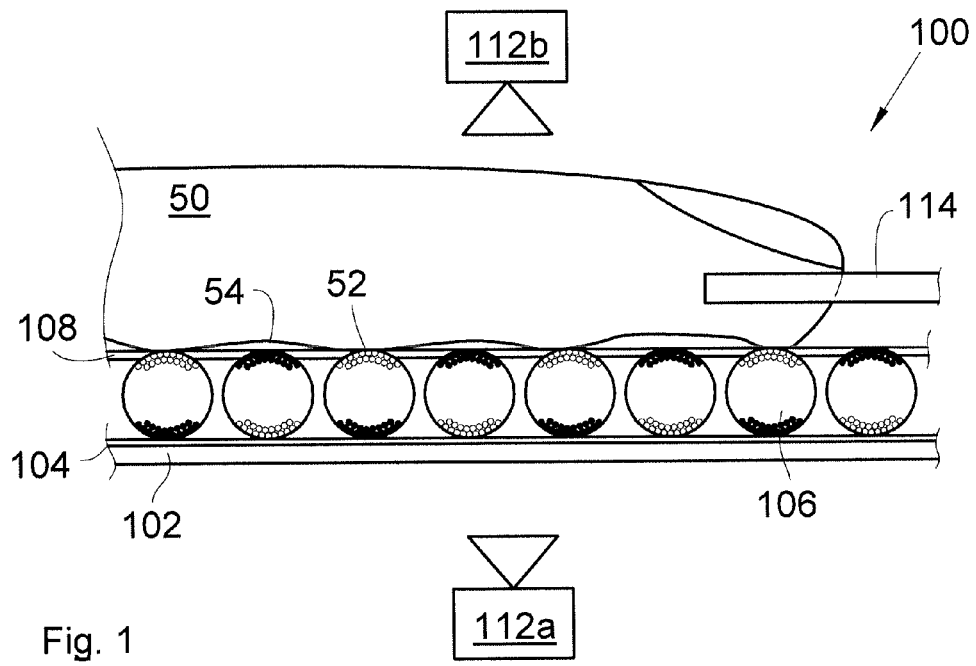

2006/0047971 A1    3/2006   Miyazaki et al.
2008/0054875 A1    3/2008   Saito
2011/0018843 A1*   1/2011   Ogawa .................... G02F 1/167
                                                                                         345/179

\* cited by examiner

DEVICE FOR CAPTURING AN IMAGE REPRESENTING A PRINT OF A PART OF THE BODY OF A PERSON

The present invention relates to a device for capturing an image representing a print, as well as a device for identifying a person using such a capture device. It finds an application in the field of biometric recognition and in particular in the field of identification by analysing the prints of a person.

Currently the capture of a print, in particular a fingerprint, consists of placing the part of the body, in particular the finger, bearing the print on a transparent window and capturing an image of said print by means of a camera through this window. The image thus captured is then compared with reference images in a database.

Depending on the light exposure, the image captured may lack contrast, which may give rise to errors during the comparison.

One object of the present invention is to propose a device for capturing a print that does not have the drawbacks of the prior art and which, in particular, enables an image to be captured with improved contrast.

To this end, a device is proposed for capturing an image representing a print of a part of the body of a person, the capture device comprising:
  a base layer,
  a reference electrode covering the base layer,
  electronic capsules fixed in the form of a matrix on the reference electrode, each electronic capsule consisting of a microcapsule filled with a liquid medium and particles with two different colours and opposite electrical charges,
  a support plate covering the electronic capsules and serving as a support for said part,
  a camera intended to take an image of the electronic capsules, and
  an active electrode intended to come into contact with said part and electrically connected to a voltage source delivering a non-zero electrical voltage.

According to a particular embodiment, the camera is above the part, and the support plate is transparent.

According to another particular embodiment, the camera is under the base layer, and the base layer and the reference electrode are transparent.

Advantageously, the capture device further comprises, for each electronic capsule, at least one electrode electrically insulated from the other electrodes and inserted in the support plate, each electrode having a first face in contact with said electronic capsule and a second face oriented outwards so as to be in contact with said part.

Advantageously, the capture device further comprises an electrically conductive reinitialisation plate intended to be applied to all the electronic capsules and subjected to a voltage of the opposite sign to that of the active electrode.

Advantageously, the base layer, the reference electrode, the support plate and any electrodes are flexible.

Advantageously, the capture device comprises an illumination system intended to illuminate the parts of the electronic capsules facing the camera.

According to a first variant, the illumination system takes the form of a set of at least one light source disposed in the vicinity of the camera and illuminating the face of the base layer opposite.

According to a second variant, the illumination system takes the form of a set of at least one light source disposed along the edge of the base layer so as to project a light flow inside said base layer.

Advantageously, the positively charged white particles are phosphorescent.

Advantageously, the positively charged white particles are fluorescent.

The invention also proposes an identification device comprising a capture device according to one of the above embodiments, a database containing reference images of prints, and a processing unit provided for comparing the image captured by the camera with the reference images of prints in the database in order to take a decision with regard to the identity of the person who has presented his part from the results of the comparisons.

Figure 2:
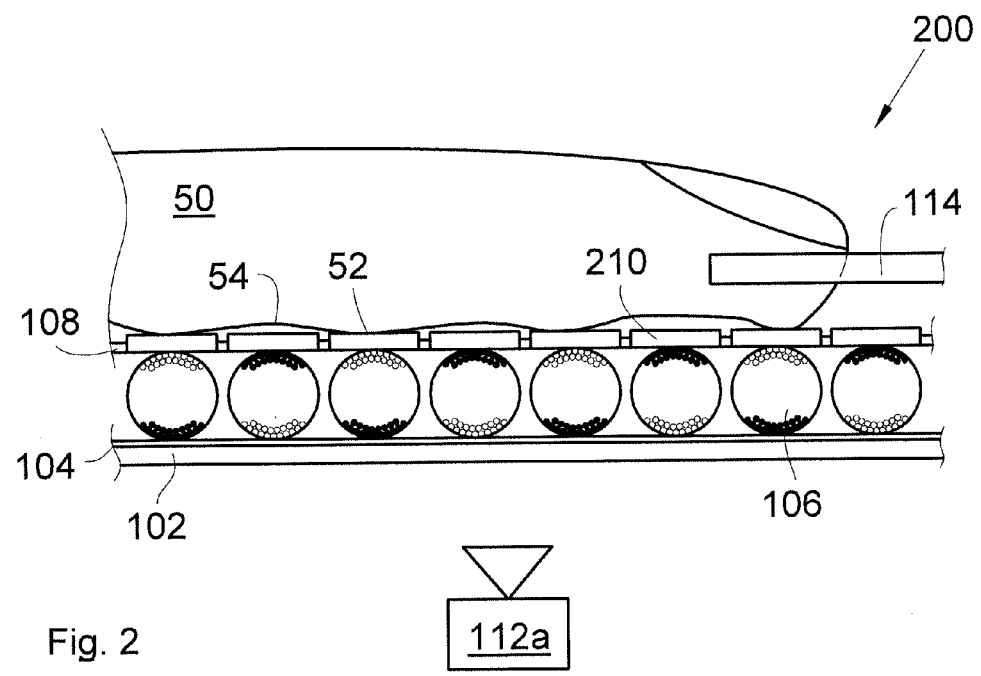
Figure 3:
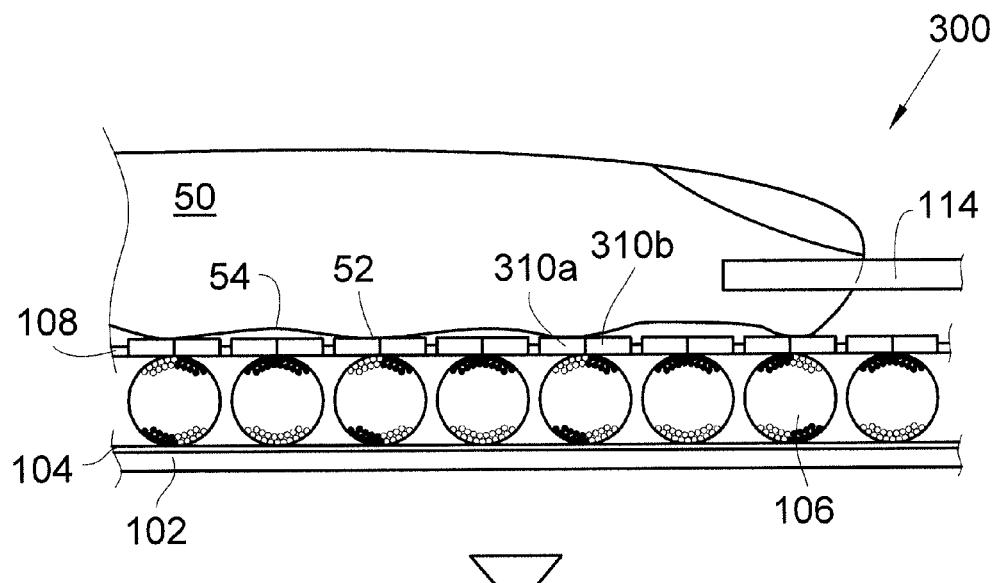
Figure 4:
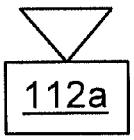
Figure 4:
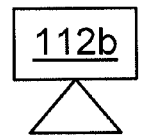
Figure 4:
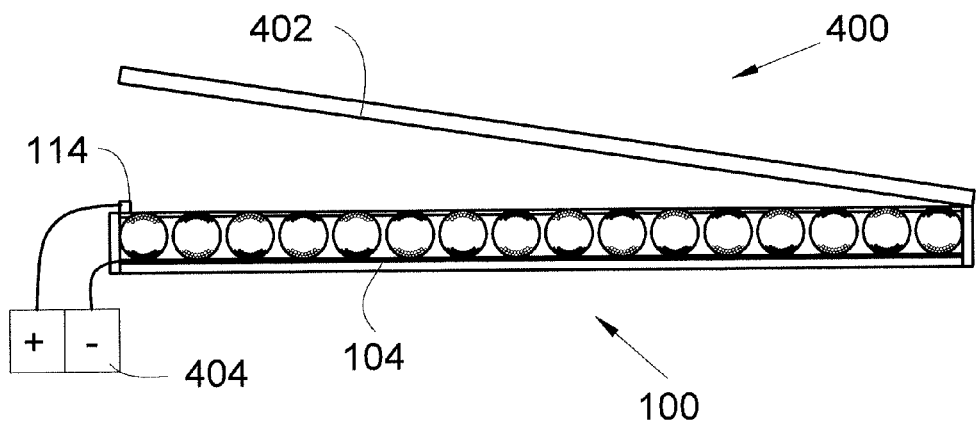

The features of the invention mentioned above, as well as others, will emerge more clearly from a reading of the following description of an example embodiment, said description being given in relation to the accompanying drawings, among which:

FIG. 1 is a schematic representation of a capture device according to a first embodiment of the invention, FIG. 2 is a schematic representation of a capture device according to a second embodiment of the invention, FIG. 3 is a schematic representation of a capture device according to a second embodiment of the invention, and FIG. 4 shows an example of use.

In the remainder of the description, the term "print" applies equally well to a fingerprint, a palm print or any other print carried by a part of the body.

In the remainder of the description, an "electronic capsule" consists of a microcapsule that preferably has a diameter of less than or equal to 50 which is filled with a liquid medium, preferably oil, and particles of two different colours, preferably white particles and black particles, the particles with different colours having opposite electrical charges, preferably the white particles are charged positively and the black particles are charged negatively.

Such electronic capsules are for example used by the company Eink in order to produce what is called an electronic ink.

FIG. 1 shows a capture device 100 according to a first embodiment of the invention. The capture device 100 is intended to capture an image representing a print carried by a part of the body of a person, here the print of a finger 50. The print of the finger 50 is produced by a series of ridges 52 and a series of valleys 54.

The capture device 100 comprises:
  a base layer 102,
  a reference electrode 104 that covers the base layer 102,
  electronic capsules 106 fixed in the form of a matrix on the reference electrode 104,
  a support plate 108 that covers the electronic capsules 106 and serves as a support for the finger 50,
  a camera 112a, 112b intended to take an image of the electronic capsules 106, and
  an active electrode 114 intended to come into contact with the finger 50 and to subject said finger 50 to a non-zero electrical voltage.

The dimensions in rows/columns of the matrix and the number of electronic capsules 106 depend on the surface area of the print.

The support plate 108 is electrically non-conductive.

The active electrode 114 is electrically connected to a voltage source delivering a non-zero electrical voltage.

The reference electrode 104 is preferably subjected to a zero voltage.

In the case of positively charged white particles and negatively charged black particles, the voltage applied to the finger 50 by the active electrode 114 is negative and preferably around −5 V.

The camera 112a, 112b may be a camera with a CCD or CMOS sensor or a flat sensor (FTF technology for example) situated directly below the base layer 102.

The functioning of the capture device 100 is as follows.

The finger 50 is placed on the support plate 108 and, by contact with the active electrode 114, is subjected to a voltage.

By contact, this voltage is transmitted to the electronic capsules 106, which are in contact with the finger 50 by means of the ridges 52.

For each electronic capsule 106, the particles of the electronic capsule 106 that carry the same electrical charge as the finger 50 are then pushed towards the reference electrode 104, while the particles that carry an electrical charge opposite to that of the finger 50 are attracted towards the finger 50.

An image of the electronic capsules 106 is then captured by the camera 112a, 112b. This image represents the ridges 52 and valleys 54 of the fingerprint 50 and the image then has an increased contrast since it is due to the difference between the particles with two different colours and is no longer due to the illumination of the finger 50.

When the camera 112b is above the finger 50, capture of the image requires first of all the removal of the finger 50, and the support plate 108 must be transparent.

When the camera 112a is under the base layer 102, the image can be captured without removing the finger 50. In this case, the base layer 102 and the reference electrode 104 are transparent.

FIG. 2 shows a capture device 200 according to a second embodiment of the invention. The capture device 200 is distinguished from the capture device 100 of the first embodiment by the fact that, for each electronic capsule 106, the capture device 200 has an electrode 210 electrically insulated from the other electrodes 210 and inserted in the support plate 108.

In this embodiment, the camera 112a is under the base layer 102, and the base layer 102 and the reference electrode 104 are transparent.

Each electrode 210 has a first face in contact with the associated electronic capsule 106 and a second face oriented outwards so as to be in contact with the finger 50, that is to say on the opposite side with respect to said electronic capsule 106. The two faces are conductive with each other.

The camera 112a captures an image of the electronic capsules 106 through the base layer 102 and the reference electrode 104.

The functioning of the capture device 200 is similar to that of the capture device 100 of the first embodiment except that the voltage to which the finger 50 is subjected is transmitted to the electronic capsules 106 through the electrodes 210 that are in contact with the finger 50 by means of the ridges 52.

FIG. 3 shows a capture device 300 according to a third embodiment of the invention. The capture device 300 is distinguished from the capture device 200 of the second embodiment through the fact that, for each electronic capsule 106, the capture device 300 has two electrodes 310a and 310b electrically insulated from each other and taking the place of the single electrode 210 of the second embodiment.

The two electrodes 310a and 310b are inserted in the support plate 108 and each have a first face in contact with said electronic capsule 106 and a second face oriented outwards so as to be in contact with the finger 50.

This embodiment improves the resolution by multiplying by two the possibilities for the particles to migrate.

When the camera 112a is under the base layer 102, the capture device 100, 200, 300 preferably comprises an illumination system intended to illuminate the parts of the electronic capsules 106 facing the camera 112a and therefore intended to appear on the captured image.

The illumination system may take the form of a set of at least one light source, each being disposed in the vicinity of the camera 112a and illuminating the face of the base layer 102 opposite.

The illumination system may take the form of a set of at least one light source, each being disposed along the edge of the base layer 102 so as to project a light flow inside said base layer 102, which then serves as a light guide for the light flow that propagates inside the base layer 102. During the propagation, a light flow that encounters an electronic capsule 106 the black particles of which are on the same side as the base layer 102 is absorbed by said black particles while a light flow that encounters an electronic capsule 106 the white particles of which are on the same side as the base layer 102 is reflected by said white particles and is thus extracted from the base layer 102 in order to illuminate the camera 112a.

In order to improve coupling, a coupling means of the optical adhesive type is disposed between the reference electrode 104 and the electronic capsules 106.

According to another variant and for all the embodiments of the invention, the positively charged white particles are phosphorescent whereas the negatively charged black particles are not. The phosphorescence illuminates the camera 112a, 112b when the image is captured. The phosphorescence is produced for example by means of a phosphorescent deposit on the particles.

According to another variant and for all the embodiments of the invention, the positively charged white particles are fluorescent whereas the negatively charged black particles are not. The fluorescence illuminates the camera 112a, 112b when the image is captured. The fluorescence is produced for example by means of a fluorescent deposit on the particles. The fluorescent deposit is recharged by means of a suitable light source, for example by a set of at least one light source, each being disposed along the edge of the base layer 102 so as to project a light flow inside said base layer 102, which then serves as a light guide for the light flow that propagates inside the base layer 102.

An identification device according to the invention comprises a capture device 100, 200, 300 according to one of the above embodiments, a database containing reference print images, and a processing unit provided for comparing the image captured by the camera 112a, 112b with the reference print images in the database and to take a decision as to the identity of the person who has presented his finger 50 from the results of the comparisons.

In order to reinitialise the electronic capsules 106, an electrically conductive reinitialisation plate is applied to all the electronic capsules 106 in place of the finger 50, and this plate is subjected to a voltage of the opposite sign to that of the active electrode 114.

To capture a large surface area of the finger 50, the capture device 100, 200, 300 is flexible so as to be able to wind around the finger 50. Thus the base layer 102, the reference electrode 104, the support plate 108 and any electrodes 210, 310a, 310b are flexible.

FIG. 4 shows a movable system 400 comprising a capture device 100 on which a reinitialisation plate 402 is pivotally mounted, and a voltage source 404, for example a battery, the negative terminal of which is connected to the reference electrode 104 and the positive terminal of which is connected to the active electrode 114.

For reinitialisation, the voltages are reversed and the reinitialisation plate 402 is pressed against the electronic capsules 106 while closing.

The camera 112*b* may for example be a mobile telephone provided with a camera which, after capture of the image of the electronic capsules 106, transmits the image to the database of the reference prints.

The movable system 400 is encircled by a metal contact and has a rectangular shape with dimensions for example of around 8 cm by 10 cm.

Naturally the present invention is not limited to the examples and embodiments described and depicted but is capable of numerous variants accessible to persons skilled in the art.

The invention claimed is:

1. A device for capturing an image representing a print of a part of a body of a person, the capture device comprising:
   a base layer,
   a reference electrode covering the base layer,
   electronic capsules fixed in the form of a matrix on the reference electrode, each electronic capsule consisting of a microcapsule filled with a liquid medium and particles with two different colours and opposite electrical charges,
   a support plate covering the electronic capsules and serving as a support for said part,
   a camera intended to take an image of the electronic capsules, and
   an active electrode intended to come into contact with said part and electrically connected to a voltage source delivering a non-zero electrical voltage.

2. The capture device of claim 1, wherein the camera is above the part, and the support plate is transparent.

3. The capture device of claim 1, wherein the camera is under the base layer, and the base layer and the reference electrode are transparent.

4. The capture device of claim 3, wherein it further comprises, for each electronic capsule, at least one electrode electrically insulated from the other electrodes and inserted in the support plate, each electrode having a first face in contact with said electronic capsule and a second face oriented outwards so as to be in contact with said part.

5. The capture device of claim 4, wherein the base layer, the reference electrode, the support plate and electrodes are flexible.

6. The capture device of claim 1, wherein it further comprises an electrically conductive reinitialisation plate intended to be applied to all the electronic capsules and subjected to a voltage of opposite sign to that of the electrode.

7. The capture device of claim 1, wherein the base layer, the reference electrode and the support plate are flexible.

8. The capture device of claim 1, wherein it comprises an illumination system intended to illuminate the parts of the electronic capsules facing the camera.

9. The capture device of claim 8, wherein the illumination system takes the form of a set of at least one light source disposed in the vicinity of the camera and illuminating the face of the base layer opposite.

10. The capture device of claim 8, wherein the illumination system takes the form of a set of at least one light source disposed along the edge of the base layer so as to project a light flow inside said base layer.

11. The capture device of claim 1, wherein the positively charged white particles are phosphorescent.

12. The capture device of claim 1, wherein the positively charged white particles are fluorescent.

13. An identification device comprising a capture device of claim 1, a database containing reference print images, and a processing unit provided for comparing the image captured by the camera with the reference print images in the database and for taking a decision as to the identity of the person who presented his part from the results of the comparisons.

\* \* \* \* \*